US005152921A

United States Patent [19]

Weber et al.

[11] Patent Number: 5,152,921

[45] Date of Patent: Oct. 6, 1992

[54] LIQUID DETERGENTS COMPOSITIONS CONTAINING 2-2-DICHLORO-5,5-DISULFODISTYRYL-BIPHENYL AS THE FLUORESCENT WHITENER

[75] Inventors: Kurt Weber, Basel, Switzerland; Claude Eckhardt, Riedisheim, France

[73] Assignee: Ciba-Geigy Corporation, Ardsley, N.Y.

[21] Appl. No.: 608,407

[22] Filed: Nov. 2, 1990

[30] Foreign Application Priority Data

Nov. 7, 1989 [CH] Switzerland ........................ 4003/89

[51] Int. Cl.[5] ........................ C07C 143/29; C11D 3/42

[52] U.S. Cl. ............................... 252/301.21; 252/549; 252/558; 8/648; 562/427; 562/84; 562/87; 585/25

[58] Field of Search .................. 252/549, 558, 301.21; 8/648; 562/427, 83, 84, 87; 585/25

[56] References Cited

U.S. PATENT DOCUMENTS 3,849,155 11/1974 Eigenmann et al. ........... 252/301.23

4,298,490 11/1981 Lange et al. ........................ 252/117

4,559,169 12/1985 Wevers .............................. 252/543

4,925,595 5/1990 Hefti et al. ..................... 252/301.21

FOREIGN PATENT DOCUMENTS 0298361 6/1988 European Pat. Off. .

2504276 1/1975 Fed. Rep. of Germany .

2076011 1/1981 United Kingdom .

OTHER PUBLICATIONS

Chem. Abstract, 110, 137,551q.

Chem. Abstract, 85, 145,183b.

Chem. Abstract, 91, 125,252u.

*Primary Examiner*—Paul Lieberman

*Assistant Examiner*—Bradley A. Swope

*Attorney, Agent, or Firm*—Edward McC. Roberts

[57] ABSTRACT

Liquid detergents containing, as the fluorescent whitener, 2,2'-dichloro-5,5'-disulfodistyrylbiphenyl, process for the preparation and use of the liquid detergent for washing and pre-treating textile fabrics; these are liquid detergents which are stable on storage, do not sediment, are stable to bleaching systems and do not form spots in the course of pre-treatment.

6 Claims, No Drawings

LIQUID DETERGENTS COMPOSITIONS CONTAINING 2-2-DICHLORO-5,5-DISULFODISTYRYLBIPHENYL AS THE FLUORESCENT WHITENER

The present invention relates to liquid detergents containing 2,2'-dichloro-5,5'-disulfodistyrylbiphenyl as the fluorescent whitener.

The use of fluorescent whiteners in liquid detergents is generally known. They exhaust onto the material to be washed during the treatment and result in elimination of the yellowish shades as a result of their special light absorption/emission property.

However, this effect is also responsible for the appearance of bleach spots if textile fabric comes into direct contact with the liquid detergent, for example in a pre-treatment. In order to solve this problem, the use of monosulfonated stilbenetriazolyl, triazine or distyrylbiphenyl whiteners is therefore suggested in EP-A 167,205. Furthermore, liquid detergents containing disulfonated distyryl whiteners are described in EP-A 0,298,361.

It has now been found, surprisingly, that the formation of bleach spots can be prevented, with an unchanged excellent whitening action, if 2,2'-dichloro-5,5'-disulfodistrylbiphenyl is incorporated into liquid detergents as the fluorescent whitener.

In addition, the whitener does not sediment and the liquid detergent is clear, i.e. without opalescence.

The invention therefore relates to liquid detergents containing fluorescent whiteners, wherein the fluorescent whitener, which is present in an amount of 0.01 to 2% by weight, preferably 0.01 to 1% by weight, consists of a disulfonic acid whitener of the formula

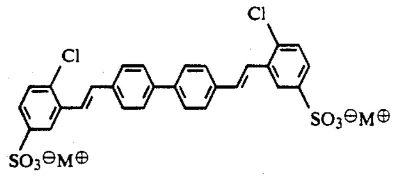

(I)

in which $M^{61}$ is hydrogen or a salt-forming cation.

Liquid detergents of particular practical interest are those containing the whitener of the formula (I) in an amount of 0.02 to 0.3% by weight.

When $M^{\oplus}$ is a salt-forming cation, it is preferably an alkali metal, such as lithium, sodium or potassium, and also substituted or unsubstituted ammonium, such as ammonium, mono-, di- or tri-ethanolammonium, mono-, di- or tri-propanolammonium or trimethylammonium or tetramethylammonium, but especially sodium.

The whiteners of the formula (I) are known, for example, from German Offenlegungsschrift 2,504,276. Their preparation is effected by known processes.

Usually, liquid detergents can contain 2–60% by weight of anionic, nonionic, cationic or zwitterionic surfactants, 3–50% by weight of builders, 25–95% by weight of solvents and 0–30% by weight of auxiliaries.

In general, the surfactant, the builder, the solvent and the auxiliaries are mixtures thereof.

Liquid detergents can contain 1–50% by weight, preferably 10–40% by weight, of anionic surfactants.

Anionic surfactants are, in particular, those of the sulfate or sulfonate type and soaps. The following may be mentioned as examples: alkylsulfates, alkylsulfonates, alkylbenzenesulfates and alkylbenzenesulfonates (in particular $C_{11}$–$C_{13}$alkylbenzenesulfonate), fatty acid monoglycerylsulfates and monoglycerylsulfonates, paraffinsulfonates, olefinsulfonates, fatty alcohol ether-sulfates, alkylglyceryl ether-sulfonates, ethoxylated alkyl ether-sulfates and alkylphenol ether-sulfates, $\alpha$-sulfofatty acids, 2-acyloxyalkane-1-sulfonic acids or $\beta$-alkyloxyalkanesulfonates. The substances can be present in the form of their alkali metal salts, in particular sodium and potassium salts, or ammonium or alkanolamine salts.

Liquid detergents can contain 1–30% by weight, preferably 4–15% by weight, of nonionic surfactants.

Nonionic surfactants can be prepared, for example, by the condensation of ethylene oxide with a hydrocarbon which carries an active hydrogen atom, for example a hydroxyl, carboxyl or amido group. Preferred compounds are $C_{12}$–$C_{15}$fatty alcohols having 4–10 mol of ethylene oxide per mol of alcohol. Other nonionic surfactants which can be used are amines and amine oxides in which the alkyl radical consists of about 8-28 carbon atoms.

Liquid detergents can contain 0–5% by weight, preferably 0.7–2% by weight, of cationic surfactants.

Examples of cationic surfactants are quaternary ammonium compounds, such as choline ester derivatives, $C_8$–$C_{16}$alkyltrimethylammonium salts, $C_8$–$C_{16}$alkyldi-(hydroxyethyl)-methylammonium salts, $C_8$–$C_{16}$alkylhydroxyethyldimethylammonium salts, $C_8$–$C_{16}$alkyloxypropyltrimethylammonium salts and $C_8$–$C_{16}$alkyloxypropyldihydroxyethylemthylammonium salts; the chlorides, bromides and methylsulfates are preferred.

Liquid detergents can contain 0–60% by weight, preferably 1–20% by weight, of zwitterionic surfactants.

Examples of zwitterionic surfactants are derivatives of secondary or tertiary amines, derivatives of heterocyclic, secondary and tertiary amines or derivatives of quaternary ammonium, quaternary phosphonium or tertiary sulfonium compounds. All these compounds contain at least one aliphatic, branched or unbranched chain containing about 3–18 carbon atoms, and at least one aliphatic substituent containing an anionic group which imparts solubility in water, for example a carboxyl, sulfonate, sulfate, phosphate or phosphonate group.

Other possible surfactants or surfactant mixtures are to be found, for example, in EP-A 0,167,205 and in U.S. Pat. Nos. 3,929,678, 4,284,532, 4,285,841, 4,321,165 and 4,507,219.

Liquid detergents can also contain 3–50% by weight, preferably 5–20% by weight, of builders.

A builder is to be understood particularly as meaning a water-soluble, inorganic or organic electrolyte, but also, for example, water-insoluble calcium ion exchange materials. The following are examples of builders: alkali metal carbonates, borates, phosphates, polyphosphates, bicarbonates, silicates, sulfates and chlorides, aminocarboxylates, aminopolyacetates, phytates, polyphosphonates, polycarboxylates (in particular citrates), nitrilotriacetic acid, organic amines and amine salts (in particular triethanolamine), sodium aluminium silicates and ethoxylated or non-ethoxylated (preferably 1–10 mol of ethylene oxide per mol of fatty acid) $C_{10}$–$C_{22}$fatty acids.

Other possible builders and mixtures of builders are described, for example, in EP-A 0,167,205 and in U.S. Pat. No. 4,321,165.

Liquid detergents can contain 25–95% by weight, preferably 30–60% by weight, of solvents.

The solvent is to be understood as meaning, in particular, water and water-miscible organic solvents. Examples of the latter are lower alcohols (in particular ethanol), diethylene glycol ether and polyethylene glycols.

The ratio between organic solvent or solvent mixture and water is generally about 1:8 to 3:1; it is also possible, however, to use only water.

Other possible solvent systems are described, for example, in EP-A 0,293,040.

Liquid detergents can also contain 0–30% by weight, preferably 2–15% by weight, of auxiliaries.

The following are examples of auxiliaries: enzymes, enzyme stabilizers, anti-foaming agents, antioxidants, preservatives, disinfectants, perfumes, dyes, complex-formers or sequestering agents, greying inhibitors, soil removers, opacifiers, hydrotropic compounds and bleaching agent systems.

Preferred bleaching agent systems are hypochlorites or substances which liberate hypochlorite, and also per-compounds, such as perborates, persulfates, perdisulfates, perphosphates and peroxocarboxylic acids, or formation components thereof.

These bleaching agent systems can be added either to the liquid detergent or to the washing bath separately.

Other examples of possible auxiliaries are to be found in German Offenlegungsschrift 2,756,573 and in EP-A 0,293,040.

A preferred liquid detergent is one which contains 0.02 to 0.3% by weight of the compound of the formula

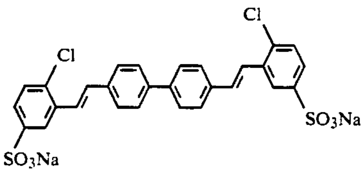

(I)

10 to 30% by weight of alkylbenzenesulfonate, 4 to 15% by weight of polyethoxy fatty alcohol, 5 to 20% by weight of builders selected from the group containing polycarboxylates, zeolites, polyphosphates and triethanolamine, a lower aliphatic alcohol, auxiliaries and water.

The whitener 2,2′-dichloro-5,5′-disulfodistyrylbiphenyl can also be employed in solid washing powders. In respect of storage and logistics costs, this is an important economic advantage. In solid detergents the whitener improves in addition to the whitening action in the washing bath, the white appearance of the washing powder.

Because of the high stability to oxidizing agents of 2,2′-dichloro-5,5′-disulfodistyrylbiphenyl, solid detergents of this type can, of course, also contain per-acid bleaching systems, without destruction of the whitener taking place during storage.

The liquid detergents can be obtained by mixing and homogenizing the fluorescent whitener, the surfactants, the builder, the solvent and, if appropriate, the auxiliaries.

The liquid detergents are used, in particular, for washing and pre-treating textile fabrics, for example fabrics containing cotton. Fabrics containing cotton are preferred.

The following examples serve to illustrate the invention; parts are parts by weight and percentages are percentages by weight; the spotting test is carried out as follows:

a) Whitener/detergent formulation:

0.1% (100% active substance) of fluorescent whitener are dissolved in a liquid detergent. 0.6 g of this whitener-containing detergent (A) is diluted with 400 ml of water (10°–12° of German hardness) at a temperature of 30° C. (wash liquor B).

b) A piece of bleached cotton fabric weighting 20 g is fastened on a stenter frame.

c) 0.6 ml of the detergent solution (A) is applied uniformly with a pipette to a previously marked, circular area (diameter 5 cm) of this cotton fabric and, after an exposure time of 30 seconds, the latter is put into the previously prepared wash liquor (B) and washed for 15 minutes at 30° C. It is then rinsed with cold water and dried at 70° C.

d) The difference in the Ganz degree of whiteness between the area of application and its surroundings is a measure of the so-called spotting behaviour (formation of bleach spots) and is determined by means of a Zeiss RFC3 photometer using a single layer of textile.

EXAMPLE 1

A liquid detergent is prepared, containing 15 parts of $C_{11}$–$C_{13}$alkylbenzenesulfonate, 14 parts of $C_{14}$–$C_{15}$polyethoxy fatty alcohol (7 ethylene oxide), 10 parts of soap, 9 parts of ethanol, 5 parts of triethanolamine, 4 parts of sodium citrate, 43 parts of water and 0.1 part of the fluorescent whitener of the formula

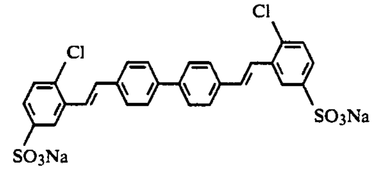

(100)

The spotting test shows only a very slight formation of bleach spots, at a very high degree of whitening.

The liquid detergent obtained is a clear agent which is very stable on storage.

COMPARISON TEST

The spotting test is carried out using the detergent from Example 1, but replacing the whitener of the formula (100) by the whitener of the formula (200) or (300) or (400).

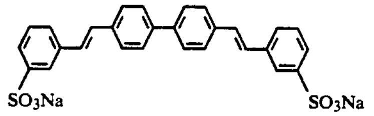

(200)

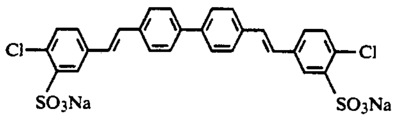

(300)

-continued

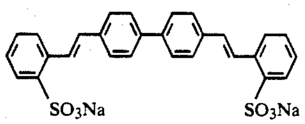

(400)

The following table shows the differences in degree of whiteness between the treated and the untreated area; the smaller the difference, the less the spotting tendency.

| Whitener | Difference in degree of whiteness |
|---|---|
| (100) | 15 |
| (200) | 32 |
| (300) | 37 |
| (400) | 45 |

EXAMPLE 2

Detergent granules having a residual moisture content of approx. 5% by weight are prepared by spray drying a slurry consisting of 1 part of water and 1 part of detergent A of the following composition 8.4 g of linear dodecylbenzenesulfonate,
3.1 g of tallow alcohol tetradecaneethylene glycol ether (14 EO),
3.7 g of sodium soap (predominantly composed of behenic acid and $C_{14}$-$C_{20}$ acids,
45.8 g of sodium tripolyphosphate,
7.9 g of sodium silicate,
2.0 g of magnesium silicate,
1.2 g of carboxymethylcellulose,
0.2 g of ethylenediamine tetraacetate,
22.2 g of sodium sulfate and
0.1 g of the compound of the formula (100), (200) or (300).

4 g of this detergent are dissolved in one litre of water (12° of German hardness) at a temperature of 45° C. After 3 minutes 50 g of cotton fabric are put into the bath and washed for 15 minutes at a temperature of 45° C., then rinsed under running water for 30 seconds and centrifuged for 30 seconds in a whizzing machine at a speed of 1000 revolutions/minute. The cotton fabric is then dried and its degree of whiteness is determined by Ganz's methods using a spectrophotometer (Zeiss RFC3).

This washing process is repeated under exactly the same conditions, but with the addition of hypochlorite, corresponding to 0.5 g of active chlorine in a litre of water, simultaneously with the detergent. After the same treatment, the degree of whiteness of the test without chlorine is compared with that using chlorine in the washing bath. The difference in degree of whiteness provides information on the stability of the whitener to hypochlorite; the smaller this difference, the less the destruction of the whitener by chlorine.

The following results are obtained:

| Whitener | Difference in degree of whiteness |
|---|---|
| (100) | 5 |
| (200) | 18 |
| (300) | 19 |

What is claimed is:

1. A liquid detergent containing 0.02 to 0.3% by weight of a fluorescent whitener of the formula

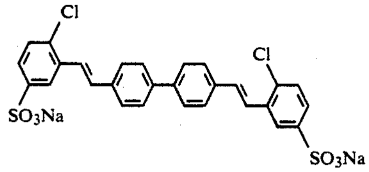

10 to 30% by weight of alkylbenzenesulfonate, 4 to 15% by weight of polyethoxy fatty alcohol, 5 to 20% by weight of a builder selected from the group consisting of polycarboxylates, zeolites, polyphosphates and triethanolamine, a lower aliphatic alcohol, auxiliaries and water.

2. A liquid detergent according to claim 1, wherein the detergent contains a bleaching system as auxiliaries.

3. A liquid detergent according to claim 2, wherein the detergent contains hypochlorite or per-compounds or formation components thereof as the bleaching system.

4. A liquid detergent according to claim 3, wherein the washing agent contains, in addition to the fluorescent whitener, anionic surfactants, a solid, water-soluble agent which releases per-acid and, if appropriate, other detergent additives.

5. The preparation of a liquid detergent according to claim 1 by mixing and homogenizing the fluorescent whitener, the surfactants, the builder, the solvent and, if appropriate, the auxiliaries.

6. The use of the liquid detergent according to claim 1, for washing and pre-treating textile fabrics.

* * * * *